US006362159B1

(12) United States Patent
Aguadisch et al.

(10) Patent No.: US 6,362,159 B1
(45) Date of Patent: Mar. 26, 2002

(54) DOMESTIC CARE PRODUCT

(75) Inventors: Louis Aguadisch, Lyons (FR); Daniel Pierre Berthod, Vlaardingen (NL); Gerrit Van Buuren, Vlaardingen (NL); Cornelis Bernard Donker, Vlaardingen (NL); Bertrand Lenoble, Seneffe (BE); Franck Renauld, Chaumount Gistoux (BE)

(73) Assignee: Unilever Home & Personal Care USA, Greenwich, CT (US)

( * ) Notice: Subject to any disclaimer, the term of this patent is extended or adjusted under 35 U.S.C. 154(b) by 0 days.

(21) Appl. No.: 09/678,083

(22) Filed: Oct. 3, 2000

(51) Int. Cl.[7] .................................................. A61K 7/46

(52) U.S. Cl. ........................................... 512/4; 510/513

(58) Field of Search ............................... 512/4; 510/513

(56) References Cited

U.S. PATENT DOCUMENTS

| | | | | |
|---|---|---|---|---|
| 4,874,129 | A | * | 10/1989 | DiSapio et al. |
| 4,973,422 | A | | 11/1990 | Schmidt |
| 6,083,900 | A | * | 7/2000 | Auguste et al. |
| 6,083,901 | A | * | 7/2000 | Perry et al. |

FOREIGN PATENT DOCUMENTS

| | | |
|---|---|---|
| DE | 10 63 309 | 8/1959 |
| EP | 273 775 | 7/1988 |
| EP | 518 555 | 12/1992 |
| EP | 495 596 | 5/1995 |
| WO | 99/21953 | 10/1997 |
| WO | 98/07405 | 2/1998 |
| WO | 98/41607 | 9/1998 |

* cited by examiner

*Primary Examiner*—Robert Dawson
*Assistant Examiner*—Marc S. Zimmer

(57) ABSTRACT

A domestic care product comprising a fragrance particle wherein the particle comprises a fragrance composition and at least one silicone polymer having a melting point of at least 10° C., provided that at least 20% of the silicone atoms in the silicone polymer have a substituent of 16 carbon atoms or more. The fragrance may be employed in relatively small proportions and yet deliver fragrance to a domestic care product over a prolonged period of time by use these silicone polymers.

14 Claims, No Drawings

DOMESTIC CARE PRODUCT

This invention is concerned with improvements in or relating to domestic care products.

In the field of domestic care products, it is a common practice to incorporate so-called functional fragrances as perfumes into the composition of the product. These fragrances are complex mixtures of selected odiferous materials. Their precise compositions are frequently held as proprietary by their suppliers. They may be viewed as a blend with a top note continuing into a middle note and on to an end note being a function of relative volatility and odour strength of the materials present in the fragrance.

The fragrances used in cleaning products serve several functions, including masking of the inherent smell of the soaps, enzymes, surfactants and the like present in them. Stability of the fragrance in the domestic care product is dependent to some extent on the reactivity with other materials present in the composition. For example, in detergents, the practices of providing highly concentrated compositions and of incorporating bleaches or enzymes into the detergent affect the stability of the hitherto preferred fragrances.

Fragrances for laundry products are chosen to provide an odour which is perceived as pleasing by the user and this benefit may manifest itself not only at the time of purchase of the laundry product, but also during storage of the product, during the wash cycle using the product, handling the wet laundry articles, during the drying process, during ironing of fabrics laundered therewith and during subsequent storage and use of the laundered fabric. In this aspect, the fragrances demonstrate the variety of the tones referred to above inasmuch as they provide an attractive odour on the shelf, mask the detergent smell, provide a fresh sensation when the washing machine is opened after a wash cycle and provide a fresh smell during ironing.

In certain conditions, the lifetime of the Head or Top Note of fragrances in powder form detergent type products is relatively short inasmuch as 50% of the fragrance has been dissipated within two weeks and effectively all of it in four weeks storage at room conditions. In order to provide a sufficient persistence of the fragrance it is common practice to incorporate the fragrance in large proportions.

To increase the effect of fragrances various techniques have been described. Some describe special fragrances such as the proaccords (WO/98/07405). Other describe special encapsulation methods. For example, WO98/41607 describes perfume particles comprising a glassy material such as hydrogenated starch hydrolysates, sucrose, glucose. U.S. Pat. No. 4,973,422 describes perfume particles with a pH sensitive coating comprising acrylic resins, cellulose acetate phthalate and cellulose acetate trimellitate.

We have now found that fragrance may be employed in relatively small proportions and yet deliver fragrance to a domestic care product by the use of certain silicone polymers that will protect the fragrance and will enable a controlled release of the fragrance over a prolonged period of time.

SUMMARY OF THE INVENTION

The present invention provides in one of its aspects a domestic care product comprising a fragrance particle wherein the fragrance particle comprises a fragrance composition and at least one silicone polymer having a melting point of at least 10° C., provided that at least 20% of the silicone atoms in the silicone polymer have a substituent of 16 carbon atoms or more.

Preferably the fragrance particle comprises a silicone polymer with a melting point of at least 10° C., preferably from 10 to 200° C., more preferably from 15 to 180° C., even more preferably from 25 to 95° C.

In a product according to the invention, the fragrance particle may comprise a cross-linked, a linear or branched organic additive that is mixed with the silicone polymer. The present invention provides in yet another of its aspects a product comprising at least one silicone polymer and a fragrance composition, the product being capable of releasing odour from the fragrance composition in the environment while it is deposited on the cleaned surface.

Preferably the fragrance particle according the invention comprises a) from 1 to 60 wt %, more preferably from 3 to 40%, even more preferably from 5 to 20 wt % of a fragrance composition;

b) from 1 to 80 wt %, more preferably from 3 to 40 wt %, even more preferably from 5 to 30 wt % at least one silicone polymer having a melting point of at least 10° C., provided that at least 20% of the silicone atoms in the silicone polymer have a substituent of 16 carbon atoms ore more;

c) an organic additive in a weight ratio of silicone polymer to organic additive from 1:99 to 100:0;

d) from 0 to 95 wt %, of a carrier material; and e) from 0 to 60 wt %, of a binder material expressed as weight percentage of the fragrance particle composition.

DETAILED DESCRIPTION OF THE INVENTION

The fragrance particle in the product according to the invention may be designed to deliver the fragrance at a desired rate at room temperature during the storage of the domestic product, and possibly at a different rate at elevated temperature or in an aqueous environment in presence of copious quantities of water such as one may find in a washing cycle whether in a machine or a manual washing activity. An additional advantage of the present invention is that the fragrance release also occurs while the fragrance particles are deposited on the cleaned surface after the cleaning process.

According to the delivery required, one may incorporate an organic additive to influence release of fragrance through the silicone polymer, to trigger release as result of temperature change, or to trigger release as a result of agitation in aqueous medium. Organic additives which may be employed in compositions sensitive to increase in temperature may include for example an organic material having a melting point of at least 10° C., Organic additives which may be used in compositions intended to release fragrance during a washing cycle include those which swell in water as hereinafter described.

The fragrance particle in the product according to the invention may also comprise a surfactant, supporting material and/or a binder.

Domestic Care Products

The fragrance particle in the product according to the invention may be adapted for use in various types of domestic care products and they are especially useful where the fragrance is to be protected from predatory ingredients of the composition. Domestic care products for the present invention are household cleaning products and laundry products and in particular fabric softeners, detergents in liquid, paste, gel or solid form (particulate, tablet, bar) and products for use in dryers such as tumble dryer sheets, refreshing or dry cleaning products. For the purpose of this patent the term "domestic care products" only describes the type of products and should not be understood to be limiting to the setting the products are used in. For example, the invention also encompasses laundry products used in an industrial setting.

The amount of fragrance particles in the domestic care product of the invention can be easily determined by the skilled person taking into account the specific type and purpose of the product and amount of fragrance in the fragrance particle. If the fragrance particle comprises a high concentration of fragrance ingredients, less particles may be used in the domestic care product. The aim is to provide an improved endurance of the fragrance. Typically the amount of fragrance particle is such that the fragrance composition is present in amounts of 0.01 to 95 wt %, preferably, 0.05 to 80wt %, more preferably, 0.1 to 70wt % by weight of the domestic care composition. For example, if the domestic care product is a laundry detergent product, the domestic care product may comprise an amount of fragrance particles to achieve an amount of 0.1–10 wt % of fragrance composition in the final domestic care product by weight of the domestic care product.

Many domestic care products incorporate surfactants and various additives and some of them may also include for example bleaches, enzymes and other aggressive ingredients as well as builders to encourage the ingredients to perform as required. For example, detergent compositions in powder form are used for washing purposes in machines for washing dishes or for laundering of textiles. These compositions generally contain organic surfactants, substantially water-insoluble micro-crystalline waxes, detergency building salts, for example phosphates and polyphosphates, silicates, such as sodium silicates, carbonates, sulphates, oxygen releasing compounds, such as sodium perborate and other bleaching agents, and zeolites, organic components such as anti-redeposition agents such as carboxy methyl cellulose (CMC), brighteners, chelating agents, such as ethylene diamine tetra-acetic acid (EDTA), nitrilotriacetic acid (NTA), enzymes and bacteriostats. Foam control agents for example a silicone antifoam compound comprising a polydiorganosiloxane and a solid silica are commonly employed. Carrier materials for these various components may be incorporated as desired.

The surfactants for these various domestic care products are those well known to the person skilled in the art and are selected from organic detergent surfactants of the anionic, cationic, non-ionic or amphoteric type, or mixtures thereof. Suitable anionic organic detergent surfactants include alkali metal soaps of higher fatty acids, alkyl aryl sulphonates, for example sodium dodecyl benzene sulphonate, long chain (fatty) alcohol sulphates, olefin sulphates and sulphonates, sulphated monoglycerides, sulphated ethers, sulpho succinates, alkane sulphonates, phosphate esters, alkyl isothionates, sucrose esters and fluor-surfactants. Suitable cationic organic detergent surfactants include alkyl-amine salts, quaternary ammonium salts, sulphonium salts and phosphonium salts. Suitable non-ionic organic surfactants include condensates of ethylene oxide with a long chain (fatty) alcohol or fatty acid, for example C14–15 alcohol, condensed with 7 moles of ethylene oxide (Dobanol 45-7), condensates of ethylene oxide with an amine or an amide, condensation products of ethylene and propylene oxides, fatty acid alkylol amides and fatty amine oxides. Suitable amphoteric organic detergent surfactants include imidazoline compounds, alkylaminoacid salts and betaines. Preferably, the domestic care product comprises 0 to 95 wt %, more preferably 1 to 90 wt % even more preferably, 2 to 80 wt % of surfactant by weight of the domestic care product.

The domestic care product may also comprise carrier particles with foam control agents, or so called antifoam granules.

Fragrance Particle Form

The fragrance particle in the domestic care product according to the invention may take any convenient form. Thus, the fragrance particle may take the form of a pellet, granule or capsule of finely divided particles or microcapsules, which may be used as a matrix type particle per se or incorporated in solid articles or in capsules, for example capsules of gelatin or silicone. Particles of the invention may be shaped as by moulding, extrusion, pelletising or granulating or in any other convenient way. Characteristics of the articles may be controlled within wide limits by appropriate selection of the components and the method of manufacture. Preferably, the fragrance particle according the invention has a volume of less than 10 $cm^3$ and preferably more than 1 $nm^3$. In some cases it may be more convenient to characterise the fragrance particles by their average particle size. In that case, the fragrance particle has an average size of more than one nm, more preferably more than one micrometer, preferably at least 2 micrometer, even more preferably at least 10 micrometer and preferably at most 500 micrometer, more preferably at most 300 micrometer, most preferably at most 200 micrometer.

Fragrance

Fragrances which may be employed in fragrance particles according to the present invention are those which can be usefully released at sufficient dosage over a required period of time from the fragrance particle. They may be selected for example from natural, essential oils or synthetic perfumes, and blends thereof. Many fragrances are polar in nature because they contain substantial amounts of alcohols and other polar compounds. Typical perfumery materials include natural oils such as lemon oil, mandarin oil, clove leaf oil, cedar wood oil, rose absolute or jasmine absolute, natural resins such as labdanum resin or olibanum resin; single perfumery chemicals which may be isolated from natural sources or manufactured synthetically, as for example alcohols such as geranoil, nerol, citronellol, linalool, tetrahydrogeranoil, beta-phenylathyl alcohol, methyl phenyl carbinol, dimethyl benzyl carbonol, menthol or cedrol; acetates and other esters derived from such alcohols; aldehydes such as citral, citronellal, hydroxycitronella, lauric aldehyde, undecylenic aldehyde, cinnamaldehyde, amyl cinnamic aldehyde, vanillin or heliotropin; acetals derived from such aldehydes; ketones such as methyl hexyl ketone, the ionones and the methylionones; phenolic compounds such as eugenol and isoeugenol; synthetic musks such as musk xylene, musk ketone and ethylene brassylate; and the like. Fragrances for use in the present invention may be those which deliver their fragrance from the fragrance particle at room conditions of temperature and humidity, those which deliver their fragrance principally in an aqueous laundry medium or those which deliver their fragrance principally upon heating during drying or ironing of the laundered textiles.

The fragrance may be a solid or liquid material and may be combined with the silicone polymer after preparation of the fragrance particle, for example by aspiration into a cellular fragrance particle, but is preferably incorporated into the fragrance particle before or during preparation of the fragrance particle. If it is intended to prepare fragrance particles by curing the silicone polymer in presence of the fragrance, it is important to ensure that the fragrance chosen does not interfere with the curing of the silicone to an unacceptable extent. In another preferred mode of preparing the articles, the fragrance is introduced to the components of or for a fragrance particle in the form a granule in which the silicone polymer comprises at least one silicone polymer according to the invention.

The proportion of the fragrance employed in a fragrance particle according to the invention is chosen in accordance with the concentration of the fragrance required to be delivered under the specified conditions and may be varied within a very wide range. The fragrance may provide a major or a minor amount of the fragrance particle. The efficient delivery achieved with articles according to the invention permits use of comparatively low dosage levels. Typically, the fragrance particle comprises from 1 to 60 wt %, more preferably from 3 to 40%, even more preferably from 5 to 20 wt % of a fragrance composition by weight of the particle composition.

Silicone Material

The silicone polymer present in the fragrance particle according to the invention are those suitable for binding, i.e., containing or entrapping, the fragrance components of the composition, provided the fragrance particle comprises at least one silicone polymer having a melting point of at least 10° C., whereby that at least 20% of the silicone atoms in the silicone polymer have a substituent of 16 carbon atoms or more.

Preferably the fragrance particle comprises a silicone polymer with a melting point of at least 10° C., preferably at most 200 ° C., more preferably from 15 to 180° C., even more preferably from 20 to 150° C., even more preferably from 25 to 120° C., most preferably in the range 35 to 95° C.

When a mixture of polymers and/or additive is used the mixture will often have a temperature range starting from a certain temperature whereby some of the components start to melt and ending at a temperature whereby all the components of the complete mixture have melted. For the purposes of this invention it should be understood that in that case the melting point refers the temperature whereby the complete mixture has melted.

The silicone polymer may provide a major or minor proportion of the fragrance particle. In the simplest form, the silicone polymer comprises a polysiloxane comprising units $R_aR'_bSiO_{4\ (a+b)/2}$ wherein R represents an organo group which may be a monovalent hydrocarbon group having up to 100 carbon atoms (for example a alkyl group or an aryl group), a halogenated group, an alkenyl group or an organofunctional group for example amino, alcohol, carboxyl, amide, phenyl, X represents an R group or a hydroxyl group, a has a value from 0 to 4, b has a value from 0 to 4 and the sum of a+b is less than 4, the polyorganosiloxane having a melting point of at least 10° C. This polyorganosiloxane may be mainly linear, or branched. When the polymer is branched, the polymer may contain an $RSiO_{3/2}$ unit or an $SiO_{4/2}$ unit. Further the polymer may be used with fillers of the type which are usually compounded in silicone such as silica.

The silicone polymer employed in the present invention comprises substituents having at least 16 carbon atoms. The preparation of such polymers has been described before for example in EP-A-495 596 and in EP-A-518 555.

Preferably, the fragrance particle according the invention comprises a silicone polymer with the following formula:

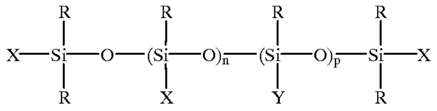

Wherein

R=$CH_3$ or X

X=an alkyl, a substituted alkyl, an alkylene group or a substituted alkylene group, an aryl group, a halogenated group, or an organofunctional group for example amino, alcohol, carboxyl, amide, phenyl, preferably with 16 to 100 carbon atoms, preferably, 18–80, more preferably 20 to 60 and most preferably 22 to 50 carbon atoms, provided that at least 20% of the silicone atoms in the silicone polymer have an alkyl substituent of 16 carbon atoms or more, Y=R or phenyl n=1 to 1000 p=0 to 1000.

Preferably, X=an alkyl, a substituted alkyl, an alkylene group or a substituted alkylene group, preferably with 16 to 100 carbon atoms, preferably, 18–80, more preferably 20 to 60 and most preferably 22 to 50 carbon atoms.

Preferably, the inventive fragrance particle comprises from 1 to 80 wt %, more preferably from 3 to 40 wt %, even more preferably from 5 to 30 wt % at least one silicone polymer by weight of the particle composition.

Organic Additive

When making fragrance particles according to the invention it is possible and preferred to incorporate one or more organic additives for modifying the rate of release of the fragrance from the silicone polymer when subjected to particular physical conditions. Such additives may be particularly beneficial for enhancing release in an aqueous environment or when heated or when compressed or any combination thereof for example, when exposed to the normal atmosphere at room temperature and atmospheric pressure and a pH of about 9, when stored within a container of the domestic care product at a pH of for example about 7–9, when subjected to an aqueous medium at a temperature in the range from 30° C. to 90° C. and a pH as found in a domestic washing machine cycle (e.g., of about 7.5 to 12), or when heated to a temperature in the range from 20° C. to 95° C. when subjected to a domestic tumble dryer environment or when pressed under an iron at a temperature in the range from 90° C. to 180° C. as in domestic ironing operation. Alternatively, the organic additive may be chosen to release the fragrance in an acidic medium or even a non-aqueous medium such as is used dry cleaning applications.

The mixture of the silicone polymer and fragrance preferably also comprise an organic additive. Preferably the organic additive has a melting point of at least 10° C., preferably at most 200° C., more preferably from 15 to 180° C., even more preferably from 20 to 150° C., even more preferably from 25 to 120° C., most preferably in the range 35 to 95° C.

Organic additives which influence the release of fragrance through the silicone may be linear, branched, saturated or unsaturated compounds and include for example alkanes, alcohols, acids, amines, surfactants and polymers such as polyisobutylene. Usually, the organic additive is selected from the group consisting of natural and synthetic organic waxes and gums, polyalkylenes and derivatives thereof. Preferably, the organic additive is a linear alkane.

For some purposes, the organic additive may comprise a solid water soluble polymeric material selected from the group consisting of water soluble polymers and copolymers or acrylic acid, methacrylic acid, acrylamide, cellulose derivatives and salts thereof, carboxymethylchitin, polyvinyl pyrrolidone, polyvinyl alcohol, ester gum, starch derivatives, polysaccharides polyethylene oxide, gelatin, collagen, carbohydrate, hyaluoronic acid, sodium alginate, gelatin gluten, natural gums and mixtures thereof. Examples of water-soluble polymeric materials include water-soluble acrylic polymeric material such as carboxyvinyl polymers (such as polyacrylic acid, polymethacrylic acid, and copolymers or partially cross-linked products thereof) and water-soluble salts thereof (such as ammonium salts and alkali metal salts, e.g. sodium salts and potassium salts), and polyacrylamide and copolymers or partially cross-linked products between polyacrylamide and the foregoing carboxyvinyl polymer, with the molecular weight being generally about 20,000 or more and preferably from about 50,000 to 15,000,000; or water soluble cellulose derivatives (such as methyl celluloses, ethyl celluloses, hydroxymethyl celluloses, hydroxypropyl methyl celluloses, and carboxymethyl celluloses), carboxymethylchitin, polyvinyl pyrrolidone, polyvinyl alcohol, ester gum, water-soluble derivatives of starch (such as hydroxypropyl starch and carboxymethyl starch), and water soluble polyethylene oxides. Examples of natural polymeric materials include hyaluronic acid, sodium alginate, ethercollagen, gelatin, gluten, gum arabic, mannan, dextran, tragacanth, amylopectin, xanthan gum, cholla gum, locust bean gum, casein, pectin, and fibrin glue.

More preferably, the organic additive is selected from the group consisting of polyethylene, polypropylene polyisobutylen, polyvinyl pyrrolidone, polyvinyl alcohol, polysaccharide, synthetic and natural wax and gum, polyethylene glycol and mixtures thereof.

Preferably, the weight ratio of silicone polymer to organic additive is from 1:99 to 100:0, preferably from 10:90 to 90:10, more preferably from 25:75 to 75:25 most preferably from 60:40 to 40:60.

If the additive comprises a surfactant, the surfactant is preferably selected from the group comprising ethoxylate alcohols, fatty alcohol sulphates, fatty ethoxylated alcohol sulphate, secondary alcohol alkanes, dodecyl benzene sulphonate cationics and mixtures thereof.

Carrier Material and Optional Ingredients

To improve the handling and processing of the fragrance particles it may be useful to use a carrier material, preferably a solid material. Supporting material or carrier material is preferably selected from the group comprising sodium tripolyphosphate, sodium silicate, sodium carbonate, sodium bicarbonate, sodium sulphate, sodium sulphite, sodium chloride, sodium citrate, sodium acetate, sodium perborate, sodium percarbonate, titanium dioxide, zeolite, layered silicate, alumina silicates, natural clays, calcium carbonate, starch and derivatives thereof, cellulose and derivatives thereof, polycarboxylate homo- and co-polymers, talc, silicas, and mixtures thereof. Carrier material may comprise 0–95%, or preferably 5–80% or more preferably, 10–70% by weight of the fragrance particle composition.

If carrier material is used it is preferably used with a binder. Preferably, binders are selected from the group comprising of polyethylene glycols, polypropylene glycols, sugars, starch and derivatives thereof, cellulose and derivatives thereof, polycarboxylate homo- and co-polymers, polyvinyl pyrrolidone, natural gums, carboxymethyl cellulose, polyvinyl alcohol and mixtures thereof. Binders are preferably present in an amount of 0–20%, more preferably 1–10% by weight of the fragrance particle composition.

If desired, in order to adjust the properties of the mixture, it may also comprise viscosity adjusting components such as fatty bases or other auxiliary agents. Examples of the fatty bases include petroleum jelly, paraffins, Plastibase 50W, (which is a mixture of 100 parts by weight of liquid paraffin and 5 parts by weight of a polyethylene of molecular weight 21,000), polyethylene glycol, various vegetable fats and oils, various animal fats and oils, waxes, unguentum simplex, hydrophilic vaseline, purified lanolin, dextrin fatty acid esters, fatty acid glycerides, fatty acids, liquid paraffin, squalane, and lanolin alcohol.

If desired other adjuvants may be incorporated in the silicone compositions for example fillers, colorants, coloured indicators, inert extenders, diluents and processing aids for example cyclic and linear polydiorganosiloxanes. The presence of some silica filler is desirable when articles of strongly elastomeric properties are required.

Preparation

The fragrance particles in the domestic care products according to the invention may be formed by any suitable technique know to the skilled person such as extrusion or granulation When producing articles by coating or granulation techniques, it is generally not possible to incorporate more than about 25% of liquid components with the solids employed in a single coating or granulated step, whereas in those cases where moulding type techniques are employed in which the solid ingredients are dispersed in liquid ingredients prior to moulding, one may employ larger proportions of the silicone.

One preferred process for preparing a fragrance particle according to the invention, comprises the steps of mixing the fragrance and the silicone polymer, and optionally an organic additive, in their liquid phase, cooling the resulting mixture, and milling the mixture into smaller particles. Another preferred process for preparing the particle according to the invention comprises the steps of mixing the fragrance and the silicone polymer, and optionally an organic additive, in their liquid phase, and depositing said mixture onto a carrier, being any of those materials recited above. The conventional procedures for making powders are particularly convenient e.g. granulation, atomisation, spray cooling, spray chilling, prilling, milling and fluid bed coating procedures. For example the fragrance in liquid form, and the silicone polymer in liquid form, may be passed into a tower and permitted to form the fragrance particle by depositing the fragrance onto the silicone polymer and a carrier material. The silicone polymer and the fragrance may be sprayed simultaneously onto a fluidised bed of carrier. Upon spraying, small liquid droplets are formed containing the silicone polymer and the fragrance. The droplets cool down as they make their way onto the bed. Thus they solidify, forming a particulate finely divided particles which are then deposited onto the carrier. The silicone polymer and the fragrance may be mixed prior to spraying, or by contacting the sprayed liquid droplets of both materials, for example by spraying the materials via separate nozzles.

Solidification of the droplets may be encouraged, for example by use of a cool air counter stream, thus reducing more quickly the temperature of the droplets. Preferably the solidification does not take place prior to the mixture being deposited onto the carrier. The finely divided particles are then collected at the bottom of the tower. In another method the silicone polymer and fragrance are sprayed simultaneously into a drum mixer containing carrier. If an organic additive is used to prepare the fragrance particle, it is preferably used in the form of a premix of the silicone polymer and organic additive. The premix of the silicone polymer and organic additive preferably has a melting point of at least 10° C., preferably at most 200 ° C., more preferably from 15 to 180° C., even more preferably from 20 to 150° C., even more preferably from 25 to 120° C., most preferably in the range 35 to 95° C. Fragrance particles so formed are generally of irregular shape. They may be sufficiently small e.g. from 10 to 100 micrometer or even 5 to 50 micrometer, so that they may be retained between the fibres of a textile during and/or after laundering. The fragrance particles may be inherently self adhesive to the textile if desired. Likewise, the fragrance particles may simply adhere to hard surfaces after cleaning.

The silicone polymer, fragrance and optionally the organic additive can be deposited onto a carrier such as sodium carbonate (light soda ash) or zeolites in a number of ways. These include depositing of a previously prepared mixture of the desired components onto the carrier which is the most preferred method. It is also possible to deposit each of the ingredients separately onto the carrier, in which case it is important that the silicone is not deposited prior to the fragrance. One particularly useful way of depositing the components onto the carrier is by spraying one or more of these onto the carrier, which may be present in a drum mixer, fluidised bed etc. If solvents are used in the process, this may be done at room temperature or at elevated temperature, which is particularly useful if one wants to evaporate some or all of any solvent used. In one process the carrier powder is mixed with the premix of all the other components of the fragrance particle, e.g. in a high shear mixer, e.g. Eirich® pan granulator, Schugi® mixer, Paxeson-Kelly® twin-core blender, Loedige® ploughshare mixer. Alternatively, an AeromaticO fluidised bed granulator or Pharma® type drum mixer may be used. The deposition may be done by pouring the mixture into the mixer, as well as spraying, as is described above.

The present invention offers numerous advantages. The silicone and other materials chosen enable simple and easily controlled methods of manufacturing fragrance release articles at room or elevated temperatures to a chosen density, size and shape and having selected combinations of properties (e.g. release rate and release profile, adhesion) without imposing severe processing conditions upon incorporation into the particle of the substance to be released, e.g. high temperatures or pressures, which might be damaging to fragrances used. The articles may be formulated to give a delivery profile predetermined by appropriate selection of the types and proportions of components and ingredients used. A particular advantage of particles according to the invention is their ability to release fragrance at a controlled rate substantially better than heretofore achieved.

All percentages used herein are expressed as percentages by weight unless otherwise indicated. All documents are incorporated herein by reference.

Except in the operating and comparative examples, or where otherwise explicitly indicated, all numbers in this description indicating amounts of material, pH, temperatures etc., ought to be understood as modified by the word "about".

Where the term comprising is used in the specification or claims, it is not intended to exclude any terms, steps or features not specifically recited.

For the purpose of the present invention any reference to average particle size refers to the D(4,3) particle size, which is a volume-weighted mean diameter as described by M. Alderliesten, Part. Part. Cyst. Charact. 8, (1991) 237–241, unless explicitly stated to the contrary. The particle size can for example be determined with a Malvern Mastersizer and preferably by using a sweep sieve.

In order that the invention may become more clear there now follows a description of non limiting examples.

EXAMPLE I

A silicone/organic additive blend is made by mixing 0.55 part of silicone polymer with 0.45 part of organic additive above the melting point. The silicone polymer with a melting point of 70 C is

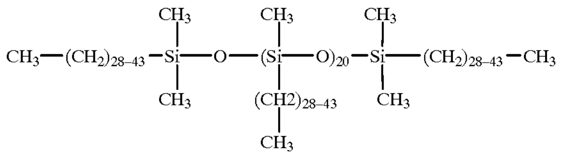

The organic additive is an organic wax ($CH_3$—$(CH_2)_{28-43}$—$CH_3$) with a melting point of 70° C. This premix of the silicone olymer and the organic wax has a melting point of 70° C. 0.50 part of fragrance is mixed with this premix at a temperature of above the melting point of the premix until a homogenous mixture is obtained. The resulting mixture is sprayed at a temperature above 70° C. onto a mixture of the carrier (zeolite) and binder (carboxy methyl cellulose). The average fragrance particle size was 5 to 30 micrometer. Fragrance particle composition:

| Ingredient | Wt % |
|---|---|
| Fragrance composition | 10 |
| Silicone/organic additive blend | 20 |
| Zeolite | 65 |
| Carboxy methyl cellulose | 5 |

The fragrance particles are used in a domestic care product such as a particulate laundry detergent composition to deliver a fragrance for a prolonged period of time.

EXAMPLE II

Similar fragrance particles were prepared as shown in Example I with the difference that light soda ash was used as carrier material.

Fragrance particle composition:

| Ingredient | Wt % |
|---|---|
| Fragrance composition | 10 |
| Silicone/organic additive blend | 20 |
| Light soda ash | 65 |
| Carboxy methyl cellulose | 5 |

The average fragrance particle size was 5 to 30 micrometer.

EXAMPLE III

In a flask equipped with a stirrer, 666 grams of a premix of the silicone polymer and the organic wax is melted at 75C. 333 grams of a fragrance composition is added to the molten premix and homogenised with rapid agitation. The homogeneous mixture is then sprayed on a cold metallic plate to allow rapid solidification. After the product has hardened, it is crushed to a small particle size using a horizontal granulator (Erweka Granulator®) equipped with a 1.25 mm grid through which the product is extruded. The obtained granules are sieved to provide fragrance particles with an average size of 400 micrometer.

EXAMPLE IV

Particulate Detergent Compositions Comprising Fragrance Particles According the Invention

| | Conventional | | Concentrated | |
|---|---|---|---|---|
| (weight %) | (1) | (2) | (3) | (4) |
| Na-LAS | 9.00 | 5.50 | 8.50 | — |
| Na-PAS | — | 1.50 | — | 8.00 |
| Ethox. Alcohol | 4.00 | 6.50 | 7.00 | 9.00 |
| Polyphosphate | 21.00 | — | — | |
| Zeolite | — | 18.00 | 28.00 | 28.00 |
| Polymer | 1.00 | 2.50 | 2.50 | 2.50 |
| Na-Citrate | — | 2.50 | 3.00 | 3.00 |
| Perborate | 15.00 | 11.00 | — | — |
| Percarbonate | — | — | 18.00 | 16.00 |
| TAED | 1.50 | 2.10 | 2.50 | 2.50 |
| Enzymes | 0.50 | 0.50 | 0.75 | 0.75 |
| Frag. particle | 0.60 | 0.60 | 1.35 | 1.35 |
| Na silicate | 6.50 | 1.50 | 5.50 | 5.50 |
| Na-Carbonate | 10.00 | 15.00 | 12.00 | 12.00 |
| Na-Sulphate | 17.00 | 23.00 | — | — |
| Minors, water | (up to 100) | | | |

EXAMPLE V

Tablet Detergent Compositions Comprising Fragrance Particles According the Invention

| (weight %) | (1) | (2) | (3) |
|---|---|---|---|
| Na-LAS | 10.50 | 9.50 | — |
| Na-PAS | — | — | 8.50 |
| Ethox. Alcohol | 4.50 | 4.00 | 4.50 |
| Polyphosphates | 45.00 | — | 45.00 |
| Zeolite | — | 38.00 | — |
| Soap | 0.50 | 0.70 | 1.50 |
| Polymer | 1.50 | — | 1.50 |
| Na-Citrate | — | 2.50 | — |
| Na-Acetate | — | 8.00 | — |
| Percarbonate | 15.00 | 15.00 | 15.00 |
| TAED | 3.00 | 5.50 | 3.00 |
| Enzymes | 1.00 | 1.00 | 1.00 |
| Fragrance particle | 1.50 | 1.50 | 1.50 |
| Na-Silicate | 3.00 | 3.50 | 3.00 |
| Na-Carbonate | — | 4.50 | 4.50 |
| Minors, water | up to 100 | up to 100 | |

EXAMPLE VI

Liquid Detergent Compositions Comprising Fragrance Particles According the Invention

| (weight %) | (1) | (2) | (3) |
|---|---|---|---|
| Na-LAS | 6.50 | 7.70 | — |
| Ethox. Alcohol | 2.50 | 2.50 | 7.00 |
| Soap | 2.00 | 1.50 | 35.00 |
| Polyphosphate | 25.00 | — | — |
| Zeolite | — | 28.00 | — |
| Bio-polymer | — | — | 0.50 |

-continued

| (weight %) | (1) | (2) | (3) |
|---|---|---|---|
| Cellulose derivative | 0.50 | 0.50 | 0.50 |
| Glycerol | 5.00 | 5.00 | — |
| Propylene glycol | — | — | 10.00 |
| Borax | 2.00 | 2.00 | 1.50 |
| Enzymes | 1.00 | 1.00 | 1.00 |
| Antifoam | 0.50 | 0.50 | 0.50 |
| Optical brightener | 0.01 | 0.01 | 0.15 |
| Fragrance particle | 0.50 | 0.50 | 0.75 |
| Water + salts | | up to 100 | |

EXAMPLE VII

General Purpose Cleaner Comprising Fragrance Particles According the Invention

| (weight %) | (1) | (2) |
|---|---|---|
| Na-LAS | 3.50 | 3.00 |
| Nonionic Surfactant | 1.50 | 0.75 |
| Soap | 0.75 | 0.50 |
| Solvent | — | 1.50 |
| Calcite | 40.00 | — |
| Na-Citrate | 5.50 | 3.50 |
| Bio-polymer | — | 0.15 |
| Fragrance particle | 0.30 | 0.30 |
| Water | up to 100 | up to 100 |

EXAMPLE VIII

Comparative Test

A particulate detergent composition comprising the fragrance particle prepared according to Example III was compared to the same particulate detergent composition without the fragrance particle whereon the perfume was sprayed. Both compositions contained 0.45 wt % perfume by weight of the total detergent composition. Terry towels (20×20 cm) were washed in a washing machine. Subsequently, the towels were dried in a room with controlled temperature and humidity. One and three days after drying the towels were tested by a trained panel of 12 people in a randomised triangular test. Towels washed by the domestic care product according to the invention showed a longer lasting fragrance with a statistical significance at the 99% confidence level after both one and three days. This experiment was carried out in triplicate whereby the washing machines were alternated in between the washes to minimise effects of individual washing machines.

What is claimed is:

1. A domestic care product comprising a fragrance particle wherein said particle comprises a fragrance composition and at least one silicone polymer having a melting point of at least 10° C., provided that at least 20% of the silicone atoms in the silicone polymer have a substituent of 16 carbon atoms or more.

2. A product according claim 1 characterised in that the alkyl substituent has from 16 to 100 carbon atoms.

3. A product according claim 2 characterised in that the silicone polymer has the following formula:

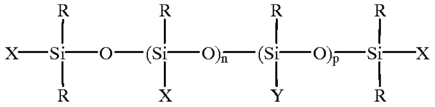

Wherein $R=CH_3$ or X

X=an alkyl, a substituted alkyl, an alkylene group or a substituted alkylene group, an aryl group, a halogenated group, or an organofunctional group, provided 20% of all silicone atoms have a group X with at least 16 carbon atoms, Y=R or phenyl n=1 to 1000 p=0 to 1000.

4. A product according to claim 1 wherein the fragrance particle further comprises an organic additive preferably with a melting point of at least 10° C.

5. A product according to claim 4 characterised in that the fragrance particle has an average size of more than 1 nm and at most 500 micrometer.

6. A product according to claim 4 characterised in that the weight ratio of silicone polymer to organic additive is from 1:99 to 100:0.

7. A product according to claim 4 characterised in that the organic additive is selected from the group consisting of alkanes, alcohols, acids, amines, surfactants, polymers and mixtures thereof.

8. A product according to claim 7 characterised in that the organic additive is preferably selected from the group consisting of natural and synthetic organic waxes and gums, polyalkylenes and derivatives thereof.

9. A product according to claim 1 characterised in that the fragrance particle comprises a carrier material selected from the group consisting of titanium dioxide, zeolite, layered silicate, alumina silicate, natural clays, calcium carbonate, starch and derivatives thereof, sugars, cellulose and derivatives thereof, polycarboxylate homo- and co-polymers, talc, silicas, alkali metal salt of tripolyphosphate, silicate, carbonate, bicarbonate, sulphate, sulphite, chloride, citrate, acetate, perborate, percarbonate and mixtures thereof.

10. A product according to claim 9 characterised in that the fragrance particle comprises a binder material preferably selected from the group consisting of a silicone, carboxymethyl cellulose, a polyvinyl alcohol, a polysaccharide or mixtures thereof.

11. A product according to claim 1 characterised in that the fragrance particle comprises a) from 1 to 60 wt %, more preferably from 3 to 40%, even more preferably from 5 to 20 wt % of a fragrance composition;

b) from 1 to 80 wt % of at least one silicone polymer;

c) an organic additive in a weight ratio of silicone polymer to organic additive from 1:99 to 100:0;

d) from 0 to 95 wt % of a carrier material; and e) from 0 to 60 wt %, of a binder, expressed as weight percentage of the fragrance particle composition.

12. A domestic care product according to claim 1 comprising 0 to 95 wt % of surfactants selected from anionic, cationic, non-ionic or amphoteric type, or mixtures thereof.

13. A process to prepare a domestic care product comprising the step of adding fragrance particles to the product whereby said particle comprises a fragrance composition and at least one silicone polymer having a melting point of at least 10° C., provided that at least 20% of the silicone atoms in the silicone polymer have a substituent of 16 carbon atoms or more.

14. A process according to claim 13 characterised in that the fragrance particle is prepared by mixing the silicone polymer, the fragrance composition and optionally an organic additive at temperature higher than the melting point of the silicone polymer and, if used, the organic additive.

* * * * *